United States Patent [19]

Lehr et al.

[11] Patent Number: 5,217,967
[45] Date of Patent: Jun. 8, 1993

[54] AGENT WITH AN ANTIDEPRESSANT ACTIVITY

[75] Inventors: Erich Lehr, Waldalgesheim; Wolf-Dietrich Bechtel, Appenheim; Astrid Schuster, Ingelheim am Rhein, all of Fed. Rep. of Germany

[73] Assignee: Boehringer Ingelheim GmbH, Ingelheim am Rhein, Fed. Rep. of Germany

[21] Appl. No.: 756,011

[22] Filed: Sep. 6, 1991

Related U.S. Application Data

[63] Continuation of Ser. No. 488,903, Mar. 6, 1990, abandoned.

[30] Foreign Application Priority Data

Mar. 6, 1990 [DE] Fed. Rep. of Germany ....... 3706399

[51] Int. Cl.$^5$ ................ A61K 31/40; A61K 31/55
[52] U.S. Cl. ...................... 514/211; 514/424; 514/922
[58] Field of Search .......... 514/211, 424, 922

Primary Examiner—S. J. Friedman
Attorney, Agent, or Firm—D. E. Frankhouser; A. S. Stempel; M-E. M. Timbers

[57] ABSTRACT

An improved process for employing tricyclic antidepressants involving co-administration of a N-benzyl-pyrrolidin-2-one.

5 Claims, No Drawings

AGENT WITH AN ANTIDEPRESSANT ACTIVITY

This is a continuation of application Ser. No. 488,903, filed Mar. 6, 1990, now abandoned.

The invention relates to an agent with an antidepressant activity containing a compound A and a compound B.

A number of tricyclic antidepressants are known from the literature, containing as their central structural element a 10,11-dihydro-dibenzo[b,f]azepine structure, a dibenzo[a,d][1,4]cycloheptadiene structure or a [10,11]-dihydro-dibenzo[b,f]oxepine structure.

On the one hand, these compounds have excellent antidepressant properties and have proved useful in therapy. On the other hand their therapeutic range of application is considerably limited by undesirable side effects, such as cardiotoxicity and proconvulsive activity.

Surprisingly, it has now been found that by combining an antidepressant of the structural type of a 10,11-dihydro-dibenzo[b,f]azepine, a dibenzo[a,d][1,4]cycloheptadiene or a [10,11-dihydro-dibenzo[b,f]oxepine (A) and optionally the pharmacologically acceptable acid addition salt thereof with a compound of the structure of an N-benzyl-pyrrolidin-2-one (B), undesirable side effects can be considerably reduced, whilst the antidepressant properties may even be increased significantly.

Compounds of structural type B include, for example, 1-benzyl-aminomethyl-pyrrolidin-2-ones and 1-pyridyl-aminomethyl-pyrrolidin-2-ones of general formula I

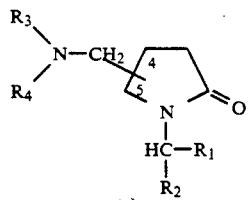

wherein
$R_1$ represents hydrogen or an alkyl group,
$R_2$ represents a phenyl group which may be mono- or disubstituted by alkoxy, fluorine, chlorine, bromine, trifluoromethyl, alkyl, hydroxy, or nitro, or it may represent a pyridyl group, and
$R_3$ represents hydrogen or an alkyl group;
$R_4$ represents hydrogen or an alkyl group or the two groups $R_3$ and $R_4$ together with the nitrogen ring which contains an O or N atom as a further heteroatom and may optionally be substituted by alkyl, preferably methyl, or form an imidazole ring, whilst the aminoalkyl group is in the 4- or 5-position and the pharmacologically acceptable acid addition salts thereof.

In general formula I the term "alkyl" indicates a straight chained or branched alkyl group having 1 to 4 carbon atoms, such as methyl, ethyl, propyl, isopropyl, n-butyl or tert.butyl, and the term "alkoxy" represents a group having 1 to 2 carbon atoms; the pyridyl ring mentioned as a definition of $R_2$ may be linked to the methylene bridge in the 2-, 3- or 4-position.

Compounds of general formula I and processes for preparing them are known from European Patent Application 136 658, which discloses the efficacy of the compounds in conditions of restricted cerebral performance.

Preferred compounds of general formula I are those wherein $R_1$ represents hydrogen, $R_2$ represents a phenyl group optionally substituted in the o-position or preferably the p-position by fluorine, chlorine, methyl or methoxy, and $R_3$ and $R_4$ represent hydrogen, methyl or ethyl or $R_3$ and $R_4$ together represent morpholine, N-methylpiperazine or pyrrolidine.

Other suitable compounds are:
1-(3,4-dimethoxybenzyl)-4-aminomethyl-pyrrolidin-2-one
1-(4-methylbenzyl)-4-aminomethyl-pyrrolidin-2-one
1-(3-trifluoromethylbenzyl)-4-aminomethyl-pyrrolidin-2-one
1-(alpha-methylbenzyl)-4-aminomethyl-pyrrolidin-2-one
1-benzyl-4-piperidinomethyl-pyrrolindin-2-one
1-benzyl-4-(N-methylpiperazinomethyl)-pyrrolindin-2-one
1-benzyl-4-(imidazol-1-yl-methyl)-pyrrolidin-2-one
1-benzyl-4-methylaminomethyl-pyrrolidin-2-one
1-(p-fluorobenzyl)-4-dimethylaminomethyl-pyrrolidin-2-one
1-(4-nitrobenzyl)-4-aminomethyl-pyrrolidin-2-one
1-(4-hydroxybenzyl)-4-aminomethyl-pyrrolidin-2-one
1-(o-chlorobenzyl)-4-aminomethyl-pyrrolidin-2-one
1-(o-chlorobenzyl)-4-dimethylaminomethyl-pyrrolidin-2-one
1-benzyl-4-isopropylaminomethyl-pyrrolidin-2-one
1-(p-methylbenzyl)-4-dimethylaminomethyl-pyrrolidin-2-one
1-benzyl-5-diethylaminomethyl-pyrrolidin-2-one
1-benzyl-5-diethylaminomethyl-pyrrolidin-2-one
1-benzyl-5-morpholinomethyl-pyrrolidin-2-one
1-benzyl-5-(4-methylpiperazino)-methyl-pyrrolidin-2-one
1-benzyl-5-pyrrolidinomethyl-pyrrolidin-2-one
1-(4-methylbenzyl-5-diethylaminomethyl-pyrrolidin-2-one
1-(4-methylbenzyl-5-diethylaminomethyl-pyrrolidin-2-one
1-(p-chlorobenzyl)-5-diethylaminomethyl-pyrrolidin-2-one
1-(p-chlorobenzyl)-5-diethylaminomethyl-pyrrolidin-2-one
1-(3,4-dichlorobenzyl)-5-diethylaminomethyl-pyrrolidin-2-one
1-(3,4-dichlorobenzyl)-5-diethylaminomethyl-pyrrolidin-2-one
1-(p-methoxybenzyl-5-dimethylaminomethyl-pyrrolidin-2-one
1-(p-methoxybenzyl)-5-diethylaminomethyl-pyrrolidin-2-one
1-benzyl-5-aminomethyl-pyrrolidin-2-one.

Preferred compounds are:
1-(4-methoxybenzyl)-4-aminomethyl-pyrrolindin-2-one
1-benzyl-4-N,N-diethylaminomethyl-pyrrolidin-2-one
1-(4-fluorobenzyl)-4-aminomethyl-pyrrolidin-2-one
1-(4-chlorobenzyl)-4-aminomethyl-pyrrolidin-2-one
1-(4-pyridylmethyl)-4-aminomethyl-pyrrolidin-2-one
1-(4-fluorobenzyl)-4-(morpholinomethyl)-pyrrolidin-2-one
1-(benzyl-4-(N-methylpiperazinylmethyl)-pyrrolidin-2-one
1-benzyl-4-methylaminomethyl-pyrrolidin-2-one.

A particularly preferred compound is
1-benzyl-4-aminomethyl-pyrrolidin-2-one

Preferred compounds of structural type A are desipramin, clomipramin, amitriptylin, nortriptylin, doxepin and maprotiline.

Imipramin, a 10,11-dihydro-N,N-dimethyl-5H-dibenz[b,f]-azepin-5-propanamine, is particularly preferred.

The agent according to the invention may contain, as a combination, one or more compounds B. The preferred combinations are those containing one compound A and one compound B. The agent according to the invention may also contain, as additional ingredients, the usual galenic excipients and carriers.

A combination of imipramin and 1-benzyl-4-aminomethyl-pyrrolidin-2-one is preferred.

The combination of conventional antidepressants (A) with 1-benzyl- or 1-pyridyl-aminomethyl-pyrrolidin-2-ones, particularly 1-benzyl-4-aminomethyl-pyrrolidin-2-one, according to the invention, substantially reduces the toxic effect of such conventional antidepressants.

A sensitive test for preclinical demonstration of antidepressant properties is the chick call test. The call frequency of isolated one day old chicks, which decreases in the course of the test, is used as an experimental behavioral model of manifestations of resignation in depression, The method has been validated by tests on numerous neurotropically active substances; it is distinguished by its highly reproducible selectivity for antidepressants which are capable of reactivating the decreased call rate as a function of dosage. [distress call activation in isolated chicks; A new behavioral model for antidepressants, E. Lehr, Psychopharmacol. 89. 21 (1986); Aktivierung des Kontaktrufens als tierexperiementelles Verhaltensmodell zur Depressionsforschung, E. Lehr, Fortschr. Neurol. Psychiat. 54, 26 (1986)]

Table I shows the pharmacological data for imipramin (compound A), 1-benzyl-4-aminomethyl-pyrrolidin-2-one (fumarate) (compound B) and the combination A+B.

TABLE I

| Test | Pharmacological Test Results | | |
|---|---|---|---|
| | Compound A | Compound B | Combination |
| Isolated chicks | 10 mg/kg i.p. | 5 mg/kg i.p. | 10 mg/kg A/ 5 mg/kg B |
| Increase in call rate in the second hour Placebo = 100% | 131% | 284% | 412% |
| Mouse | | | |
| Inhibition of ptosis induced by tetrabenazine | 3 mg/kg p.o. | 3.5 mg/kg p.o. | 3 mg/kg A + 3.5 mg/kg B |
| Control without tetrabenazine = 100% | 12% | 48% | 88% |

The combination according to the invention was tested for possible potentiation of the toxic activity after intravenous administration to mice.

Test Objective

To determine the behavioral changes, symptoms of toxicity and possibly the target organs of the toxic activity after the administration, one directly after the other, of sublethal doses of imipramin HCl and 1-benzyl-4-aminomethylpyrrolidin-2-one FU, and to detect any potentiation of the toxic activity.

| Test animals: | | |
|---|---|---|
| Albino mice of the Chbb: NMRI strain | | |
| Age at start of text: | m | 40–46 days |
| | f | 40–46 days |
| Weight (averages at start of test): | m | about 27 g |
| | f | about 24 g |

A 2% solution of 1-benzyl-4-aminomethyl-pyrrolidin-2-one fumarate and a 0.25% imipramin solution (pH=6.2) were used. The test results as shown in Table II.

TABLE II

| Group (m and f) | Test substance | Dosage | Lethality dead/treated animals |
|---|---|---|---|
| 1 | 1-benzyl-4-aminomethyl-pyrrolidin-2-one FU | 100 | 0/10 |
| 2 | imipramin-HCl | 12.5 | 0/10 |
| 3* | imipramin-HCL + 1-benzyl-4-aminomethyl pyrrolidin-2-one FU | 12.5 100 | 0/10 |

*The animals in group 3 were treated first with imipramin and then, immediately afterwards (about 10–15 seconds later), with 1-benzyl-4-aminomethyl-pyrrolidin-2-one FU.

Bases for Dosage

The $LD_{50}$ i.v. in the mouse for imipramin is 21 or 36 mg/kg according to sources in the literature (Archives International de Pharmacodynamie t de Therapie, 144, 481, 1963 or 245, 283, 1980). In a preliminary test, one of 4 treated animals died at a dosage of 16 mg/kg, whereas at a dosage of 12.5 mg/kg, therefore, some activity but no deaths can be expected.

By simultaneous administration of imipramin and 1-benzyl-4-aminomethyl-pyrrolidin-2-one FU in the maximum non-lethal dosage, which is in the region of half the $LD_{50}$ of the individual substances or may even be above this, it was shown, however, that the combination according to the invention does not result in a potentiation of the toxicity. The antagonist activity in the toxic dosage range of imipramin after intravenous administration of the combination to mice was also tested.

Test Objective

To determine the behavioral changes, toxic symptoms and possibly target organs after the administration, one after another, of sublethal doses of 1-benzyl-4-aminomethyl-pyrrolidin-2-one FU and lethal doses of imipramin HCl, and to detect any antagonist activity. The test results are shown in Table III.

Test Solutions

The test substances were dissolved in 0.9% NaCl solution.

1.5% 1-benzyl-4-aminomethyl-pyrrolidin-2-one FU solutions (pH=6.4) and 0.5% imipramin solutions (pH=5.9) were used.

TABLE III

| Group (m and F) | 1-Benzyl-4-aminomethyl-pyrrolidin-2-one FU mg/kg | Imipramin mg/kg | Lethality dead/treated animals |
|---|---|---|---|
| 1 | — | 25 | 4/10 |

TABLE III-continued

| Group (m and F) | 1-Benzyl-4-aminomethyl-pyrrolidin-2-one FU mg/kg | Imipramin mg/kg | Lethality dead/treated animals |
|---|---|---|---|
| 2** | 75 | 25 | 2/10 |

**The animals in Group 2 were treated first with 1-benzyl-4-aminomethyl-pyrrolidin-2-one FU and immediately afterwards (about 10 to 15 seconds later) with imipramin.

The $LD_{50}$ i.v. in the mouse for imipramin is 21 or 36 mg/kg according to sources in the literature (see above). The dosage of 12.5 mg/kg proved to be the maximum non-lethal effect, as confirmed by the test results.

Intravenous administration of a sublethal dose of 1-benzyl-4-aminomethyl-pyrrolidin-2-one FU and a certainly lethal dose of imipramin, immediately after one another, surprisingly resulted in a reduced mortality rate in the animals.

The test results show that the toxic effect of imipramin is reduced after the animals have been pretreated with 1-benzyl-4-aminomethyl-pyrrolidin-2-one.

The data contained in the Tables indicate a clear synergism of the combination according to the invention, which indicates that the combination is clearly superior in its antidepressant activity whilst simultaneously reducing the undesirable side effects compared with the individual compounds.

Processes for preparing compounds of structural type A are known in the art. Processes for preparing compounds of general formula I and the pharmacologically acceptable acid addition salts thereof are also known and are described in European Patent Application 136 658, to which reference is hereby made.

The combination [A+B] according to the invention may be used either on its own or possibly further combined with other pharmacologically active substances. Suitable forms for administration are, for example, tablets, capsules, suppositories, solutions, syrups, emulsions or dispersible powders. Corresponding tablets may be produced, for example, by mixing the active substance or substances with known excipients, e.g. inert diluents such as calcium carbonate, calcium phosphate or lactose, disintegrants such as corn starch or alginic acid, binders such as starch or gelatine, lubricants such as magnesium stearate or talc and/or agents for obtaining delayed release such as carboxypolymethylene, carboxymethylcellulose, cellulose acetate phthalate or polyvinyl acetate. The tablets may also consist of several layers.

Coated tablets may be produced accordingly by coating cores made in the same way as the tablets with the substances normally used for table coating, such as collidone or shellac, gum arabic, talc, titanium dioxide or sugar. In order to obtain delayed release or prevent incompatibilities, the core may also consist of several layers. Similarly, the tablet coating may consist of several layers in order to obtain delayed release, and the excipients mentioned above for the tablets may be used.

Syrups of the active substances or combinations of active substances according to the invention may additionally contain sweeteners such as saccharin, cyclamate, glycerol or sugar and a flavour-enhancing agent, e.g. a flavouring such as vanilla or orange extract. They may also contain suspension adjuvants or thickeners such as sodium carboxymethylcellulose, wetting agents, e.g. condensation products of fatty alcohols with ethylene oxide, or preservatives such as p-hydroxybenzoates.

Injection solutions are prepared in the usual way, e.g. by adding preservatives such as p-hydroxybenzoates or stabilizers such as alkali metal salts or ethylenediamine tetraacetic acid and transferring the resulting solutions into injection vials or ampoules.

Capsules containing a combination of active substances according to the invention may be prepared, for example, by mixing the active substances with inert carriers such as lactose or sorbitol and encapsulating the mixture in gelatine capsules. Suitable suppositories may be produced, for example, by mixing with suitable carriers such as neutral fats or polyethylene glycol or the derivatives thereof.

The dosage for therapeutically effective quantity of the combination is generally between 5 and 500 mg, preferably between 20 and 200 mg per single dose.

The Examples which follow illustrate the invention without restricting its scope:

EXAMPLE 1

1-benzyl-4-aminomethyl-pyrrolidin-2-one 54 g (0.16 mol) of 4-phthalimidomethyl-1-benzyl-pyrrolidin-2-one are stirred into 1.3 l of ethyl alcohol after the addition of 32 g of hydrazine hydrate for 4 hours at room temperature. The precipitate (phthalic acid hydrazide) is removed by suction filtering the filtrate is evaporated down. 500 ml of methylene choloride are added to the residue which is then extracted three times with 100 ml of water. The organic phase is dried and evaporated down. The residue remaining is dissolved in 500 ml of methanol and 20 g (0.17 mol) of solid fumaric acid are added in batches thereto, with stirring, at boiling temperature. As the mixture cools, colorless crystals are precipitated, which are then suction filtered and washed with methanol and ether.

Yield: 20–25 g (48–60% of theory),

M.p.: 209°–211° C.

The compound contains ½ mol of fumaric acid.

The starting material is obtained as follows:

a) 94 g (0.46 mol) of 1-benzyl-4-hydroxymethyl-pyrrolidin-2-one are stirred with 700 ml of methylene chloride and 40 ml )0.54 mol) of thionyl chloride for 25 hours, whilst refluxing, and the reaction mixture is then neutralized with dilute ammonia, with cooling. After separation, drying and evaporation, 85–90 g of a dark oil remain, which is used directly in the rest of the reaction.

b) 43.5 g (0.195 mol) of crude 1-benzyl-4-chloromethyl-pyrrolidin-2-one, 36 g (0.195 mol) of potassium phthalimide and 700 ml of dimethylformamide are refluxed for 2 hours. The reaction mixture is then evaporated down in vacuo and the residue is taken up in methylene chloride. This is extracted several times with water, the organic phase is dried and after chromatography on $SiO_2$, 45 g (70% of theory) of the phthalimido compound are obtained, m.p. 108°–109° C.

EXAMPLE 2

1-benzyl-4-aminomethyl-pyrrolidin-2-one a) 58 g (0.29 mol) of 1-benzyl-4-nitrilo-pyrrolidin-2-one are dissolved in methanol and subjected to catalytic hydrogenation with the addition of liquid ammonia on Raney nickel. After the reaction solution has been evaporated down, the residue is dissolved in methanol, filtered to remove any traces of catalyst and, after heating to about 50° C., combined with 17 g of fumaric acid. The fumaric acid briefly goes into solution when stirred, then the 1-benzyl-4-aminomethylpyrrolidin-2-one fumarate begins to crystallize out.

Yield: 68 g (=91% of theory); m.p. 192°-194° C.

b) The nitrilo compound is obtained in a 96% yield from the corresponding amide, m.p. 162°-166° C., by dehydration using POCl₃ in dimethylformamide at about 60° C., in the form of an oil.

EXAMPLE 3

Racemate splitting of 1-benzyl-4-aminomethyl-pyrrolidin-2-one a) 24.0 g (0.117 mol) of 1-benzyl-4-aminomethylpyrrolidin-2-one are dissolved in 200 ml of hot methanol and 17.6 g (0.117 mol) of L(+)-tartaric acid are also dissolved in 200 ml of hot methanol. The two solutions are combined and left to cool to room temperature with stirring, whereupon the salt crystallizes out. The crystals are suction filtered whilst cold, rinsed with cold methanol and dried.

Yield: 18.0 g 4-aminomethyl-pyrrolidin-2-one tartrate, m.p. 204°-206° C. (from methanol), alpha$_D$= −6.3 (c=1.0; water)- b) In order to convert the tartrate into the base the tartrate is dissolved cold in 20 ml of water and 10 ml of concentrated sodium hydroxide solution, extracted three times with methylene chloride, the combined methylene chloride phases are dried over MgSO₄ and the solvent is removed in vacuo. The (−)-4-aminomethyl-1-benzyl-pyrrolidin-2-one is obtained, alpha$_D$−8.4° (c=1.0; water).

c) The mother liquors which occur during the working up described in paragraph a) are evaporated down in vacuo. 38.0 g of the tartrate are obtained, which is taken up cold in 140 ml of water and 50 ml of concentrated sodium hydroxide solution and extracted three times with methylene chloride. The combined methylene phases are dried over MgSO₄ and the solvent is removed in vacuo. 19.3 g of base are obtained which is converted into the tartrate with D-(−)-tartaric acid, as described in paragraph a). Yield: 19.0 g, m.p. 204°-205° C.

d) The conversion of the tartrate into the base is carried out as described in b). 5.7 g of (+)-4-aminomethyl-1-benzyl-pyrrolidin-2-one are obtained, with a rotary value alpha$_D$=8.4° (c=1.0; water).

| Pharmaceutical formulation examples | |
|---|---|
| A) Tablets | per tablet |
| Active substance A + B | 100 mg |
| Lactose (powdered) | 140 mg |
| Corn starch | 240 mg |
| Polyvinylpyrrolidone | 15 mg |
| Magnesium stearate | 5 mg |
| | 500 mg |

The finely ground active ingredient, lactose and pat of the corn starch are mixed together. The mixture is screened and then moistened with a solution of polyvinylpyrrolidone in water, kneaded, granulated whilst moist and then dried. The granulate, the remaining corn starch and the magnesium stearate are screened and mixed together. The mixture is compressed to form tablets of suitable shape and size.

| B) Tablets | per tablet |
|---|---|
| Active substance A + B | 80 mg |
| Corn starch | 190 mg |
| Lactose | 55 mg |
| Microcrystalline cellulose | 35 mg |
| Polyvinylpyrrolidone | 15 mg |
| Sodium carboxymethyl starch | 23 mg |
| Magnesium stearate | 2 mg |
| | 400 mg |

The finely ground active substance, some of the corn starch, lactose, microcrystalline cellulose and polyvinylpyrrolidone are mixed together, the mixture is screened and processed with the remaining corn starch and water to form a granulate which is dried and screened. The sodium carboxymethyl starch and the magnesium stearate are added and the mixture is compressed to form tablets of suitable size.

| C) Ampoules | |
|---|---|
| 1-benzyl-4-aminomethyl-pyrrolidin-2-on fumarate | 50.0 mg |
| Imipramin | 25.0 mg |
| Sodium chloride | 10.0 mg |
| Doubly distilled water q.s. ad | 1.0 ml |

Method

The active substance and sodium chloride as dissolved in doubly distilled water and the solution is transferred into ampoules under sterile conditions.

| D) Drops | |
|---|---|
| 1-benzyl-4-aminomethyl-pyrrolidin-2-one fumarate | 5.0 mg |
| Imipramin | 2.5 mg |
| methyl p-hydroxybenzoate | 0.1 g |
| propyl p-hydroxybenzoate | 0.1 g |
| demineralized water q.s. ad | 100.0 ml |

Method

The active substance and preservatives are dissolved in demineralized water and the solution is filtered and transferred into vials each containing 100 ml.

What is claimed is:

1. A process for treating depression in a warm-blooded animal which comprises the administration to said warm-blooded of an antidepressant-inducing amount of a tricyclic antidepressant of the structural type 10,11-dihydro-dibenzo [f,f]-azepine, dibenzo[a,d][1,4]cycloheptadiene or [10,11]-dihydro-dibenzo[b,f]oxepine, with an amount of a compound of formula I

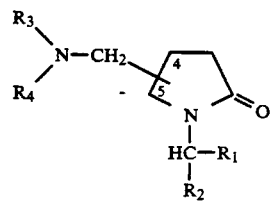

(I)

wherein
R₁ is hydrogen or alkyl, $R_2$ is phenyl, which may be mono- or di-substituted by alkoxy, fluorine, chlorine, bromine, trifluoromethyl, alkyl, hydroxy, or nitro, or $R_2$ is pyridyl, and $R_3$ is hydrogen or alkyl, and $R_4$ is hydrogen or alkyl, or a pharmacologically acceptable salt thereof, sufficient to lessen or reduce the toxic effects of the tricyclic antidepressant.

2. A pharmaceutical composition of matter comprising an antidepressant inducing amount for a warm-blooded animal of a tricyclic antidepressant of the structural type 10,11-dihydro-dibenzo[b,f]-azepine, dibenzo[a,d][1,4]-cycloheptadiene or [10,11]-dihydro-dibenzo-[b,f]oxepine or a pharmaceutically acceptable salt thereof and an amount of a compound of formula I

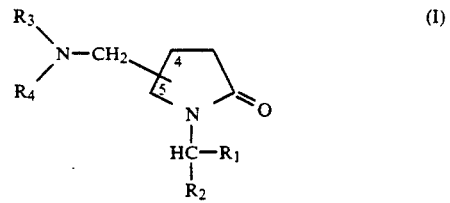

wherein
 $R_1$ is hydrogen or alkyl,
 $R_2$ is phenyl which may be mono- or di-substituted by alkoxy, fluorine, chlorine, bromine, trifluoromethyl, alkyl, hydroxy or nitro, or $R_2$ is pyridyl,
 $R_3$ is hydrogen or alkyl; and
 $R_4$ is hydrogen or alkyl, or a pharmacologically acceptable salt thereof, sufficient to lessen or reduce the toxic effects of the tricyclic antidepressant.

3. The composition of matter as recited in claim 2, characterized in that the antidepressant is desipramin, clomipramin, amitryptylin, nortriptylin, doxepin, imipramin or maprotiline.

4. The composition of matter as recited in claim 2, characterized in that it comprises a compound of general formula I wherein $R_1$ is hydrogen, $R_2$ is phenyl optionally substituted in the o- or p-position by fluorine, chlorine, methyl or methoxy and $R_3$ and $R_4$ are hydrogen, methyl or ethyl.

5. The composition of matter as recited in claim 2, characterized in that it comprises imipramine and 1-benzyl-4-aminomethyl-pyrrolidin-2-one, or the pharmaceutically acceptable salts thereof.

* * * * *